(12) United States Patent
Celermajer

(10) Patent No.: US 10,398,421 B2
(45) Date of Patent: Sep. 3, 2019

(54) DEVICES AND METHODS FOR THE TREATMENT OF HEART FAILURE

(71) Applicant: DC Devices Pty Ltd, Vaucluse NSW (AU)

(72) Inventor: David Stephen Celermajer, Vaucluse (AU)

(73) Assignee: DC Devices Pty. Ltd., Vaucluse (AU)

( * ) Notice: Subject to any disclaimer, the term of this patent is extended or adjusted under 35 U.S.C. 154(b) by 0 days.

(21) Appl. No.: 14/281,701

(22) Filed: May 19, 2014

(65) Prior Publication Data

US 2014/0257167 A1    Sep. 11, 2014

Related U.S. Application Data

(63) Continuation of application No. 12/447,617, filed as application No. PCT/AU2007/001704 on Nov. 7, 2007.

(30) Foreign Application Priority Data

Nov. 7, 2006    (AU) ................................ 2006906202

(51) Int. Cl.
*A61F 2/24*    (2006.01)
*A61B 17/02*    (2006.01)
(Continued)

(52) U.S. Cl.
CPC .......... *A61B 17/02* (2013.01); *A61B 17/0057* (2013.01); *A61F 2/06* (2013.01);
(Continued)

(58) Field of Classification Search
CPC ....................................................... A61F 2/24
(Continued)

(56) References Cited

U.S. PATENT DOCUMENTS

| 3,874,388 A | 4/1975 | King et al. |
| 4,018,228 A | 4/1977 | Goosen |

(Continued)

FOREIGN PATENT DOCUMENTS

| CN | 1218379 A | 6/1999 |
| CN | 1556719 A | 12/2004 |

(Continued)

OTHER PUBLICATIONS

Ad et al.; A one way valved atrial septal patch: A new surgical technique and its clinical application; The Journal of Thoracic and Cardiovascular Surgery; 111; pp. 841-848; Apr. 1996.

(Continued)

*Primary Examiner* — Matthew W Schall
(74) *Attorney, Agent, or Firm* — Shay Glenn LLP

(57) ABSTRACT

A device for treating a heart condition in a patient. The device has a body adapted and configured to self-expand from a radially collapsed configuration to an expanded configuration. In its expanded configuration, the device has a first section at a first end, a second section at a second end and a central portion extending between the first and second sections, the first and second sections each having diameters that increase with distance from the central portion toward the first and second ends, respectively. The body is configured to be delivered percutaneously to a patient's heart and allowed to self-expand in an opening in a septum of the heart to dispose the first end in the left atrium, the second end in the right atrium and the central portion in the opening to permit blood to flow through the body from the left atrium to the right atrium.

8 Claims, 14 Drawing Sheets

(51) Int. Cl.
*A61B 17/00* (2006.01)
*A61F 2/06* (2013.01)
*A61M 27/00* (2006.01)

(52) U.S. Cl.
CPC ............. *A61F 2/24* (2013.01); *A61F 2/2412* (2013.01); *A61F 2/2442* (2013.01); *A61F 2/2475* (2013.01); *A61M 27/002* (2013.01); *A61B 2017/00252* (2013.01); *A61B 2017/00575* (2013.01); *A61B 2017/00592* (2013.01); *A61B 2017/00606* (2013.01); *A61B 2017/00867* (2013.01); *A61B 2017/0237* (2013.01)

(58) Field of Classification Search
USPC ....................................................... 623/1.26
See application file for complete search history.

(56) References Cited

U.S. PATENT DOCUMENTS

| | | | |
|---|---|---|---|
| 4,373,216 A | 2/1983 | Klawitter | |
| 4,491,986 A | 1/1985 | Gabbay | |
| 4,705,507 A | 11/1987 | Boyles | |
| 5,100,423 A | 3/1992 | Fearnot | |
| 5,108,420 A | 4/1992 | Marks | |
| 5,171,233 A | 12/1992 | Amplatz et al. | |
| 5,284,488 A | 2/1994 | Sideris | |
| 5,332,402 A | 7/1994 | Teitelbaum | |
| 5,334,217 A | 8/1994 | Das | |
| 5,413,599 A | 5/1995 | Imachi et al. | |
| 5,429,144 A | 7/1995 | Wilk | |
| 5,433,727 A | 7/1995 | Sideris | |
| 5,464,449 A | 11/1995 | Ryan et al. | |
| 5,478,353 A | 12/1995 | Yoon | |
| 5,556,386 A | 9/1996 | Todd | |
| 5,556,408 A | 9/1996 | Farhat | |
| 5,693,090 A | 12/1997 | Unsworth et al. | |
| 5,702,412 A | 12/1997 | Popov et al. | |
| 5,725,552 A | 3/1998 | Kotula et al. | |
| 5,741,297 A | 4/1998 | Simon | |
| 5,824,071 A | 10/1998 | Nelson et al. | |
| 5,846,261 A * | 12/1998 | Kotula ............... A61B 17/0057 606/213 | |
| 5,876,436 A | 3/1999 | Vanney et al. | |
| 5,893,369 A | 4/1999 | Lemole | |
| 5,944,738 A | 8/1999 | Amplatz et al. | |
| 5,964,754 A | 10/1999 | Osypka | |
| 6,050,936 A | 4/2000 | Schweich et al. | |
| 6,059,827 A | 5/2000 | Fenton | |
| 6,068,635 A | 5/2000 | Gianotti | |
| 6,120,534 A | 9/2000 | Ruiz | |
| 6,123,682 A | 9/2000 | Knudson et al. | |
| 6,123,715 A | 9/2000 | Amplatz | |
| 6,152,937 A | 11/2000 | Peterson et al. | |
| 6,156,055 A | 12/2000 | Ravenscroft | |
| 6,168,622 B1 | 1/2001 | Mazzocchi | |
| 6,190,353 B1 | 2/2001 | Makower et al. | |
| 6,193,734 B1 | 2/2001 | Bolduc et al. | |
| 6,210,338 B1 | 4/2001 | Afremov et al. | |
| 6,214,029 B1 | 4/2001 | Thill et al. | |
| 6,241,678 B1 | 6/2001 | Afremov et al. | |
| 6,258,119 B1 | 7/2001 | Hussein et al. | |
| 6,286,512 B1 | 9/2001 | Loeb et al. | |
| 6,334,864 B1 | 1/2002 | Amplatz et al. | |
| 6,350,277 B1 | 2/2002 | Kocur | |
| 6,355,052 B1 | 3/2002 | Neuss et al. | |
| 6,355,056 B1 | 3/2002 | Pinheiro | |
| 6,357,735 B2 | 3/2002 | Haverinen | |
| 6,383,195 B1 | 5/2002 | Richard | |
| 6,391,036 B1 | 5/2002 | Berg et al. | |
| 6,395,017 B1 | 5/2002 | Dwyer et al. | |
| 6,402,777 B1 | 6/2002 | Globerman et al. | |
| 6,409,716 B1 | 6/2002 | Sahatjian et al. | |
| 6,440,152 B1 | 8/2002 | Gainor et al. | |
| 6,454,795 B1 | 9/2002 | Chuter | |
| 6,458,153 B1 | 10/2002 | Bailey et al. | |
| 6,468,301 B1 | 10/2002 | Amplatz et al. | |
| 6,468,303 B1 | 10/2002 | Amplatz et al. | |
| 6,527,746 B1 | 3/2003 | Oslund et al. | |
| 6,572,652 B2 | 6/2003 | Shaknovich | |
| 6,579,311 B1 | 6/2003 | Makower | |
| 6,599,308 B2 | 7/2003 | Amplatz | |
| 6,626,936 B2 | 9/2003 | Stinson | |
| 6,638,257 B2 | 10/2003 | Amplatz | |
| 6,645,143 B2 | 11/2003 | Vantassel et al. | |
| 6,666,885 B2 | 12/2003 | Moe | |
| 6,699,256 B1 | 3/2004 | Logan et al. | |
| 6,712,836 B1 | 3/2004 | Berg et al. | |
| 6,719,768 B1 | 4/2004 | Cole et al. | |
| 6,719,934 B2 | 4/2004 | Stinson | |
| 6,837,901 B2 | 1/2005 | Rabkin et al. | |
| 6,866,679 B2 | 3/2005 | Kusleika | |
| 6,911,037 B2 | 6/2005 | Gainor et al. | |
| 6,913,614 B2 | 7/2005 | Marino et al. | |
| 6,932,837 B2 | 8/2005 | Amplatz et al. | |
| 6,936,058 B2 | 8/2005 | Forde et al. | |
| 6,979,343 B2 | 12/2005 | Russo et al. | |
| 7,033,372 B1 | 4/2006 | Cahalan | |
| 7,037,329 B2 | 5/2006 | Martin | |
| 7,044,134 B2 | 5/2006 | Khairkhahan et al. | |
| 7,097,653 B2 | 8/2006 | Freudenthal et al. | |
| 7,105,024 B2 | 9/2006 | Richelsoph | |
| 7,144,410 B2 | 12/2006 | Marino et al. | |
| 7,226,466 B2 | 6/2007 | Opolski | |
| 7,309,341 B2 | 12/2007 | Ortiz et al. | |
| 7,317,951 B2 | 1/2008 | Schneider et al. | |
| 7,338,514 B2 | 3/2008 | Wahr et al. | |
| 7,350,995 B1 | 4/2008 | Rhodes | |
| 7,419,498 B2 | 9/2008 | Opolski et al. | |
| 7,445,630 B2 | 11/2008 | Lashinski et al. | |
| 7,473,266 B2 | 1/2009 | Glaser | |
| 7,485,141 B2 | 2/2009 | Majercak et al. | |
| 7,530,995 B2 | 5/2009 | Quijano et al. | |
| 7,611,534 B2 | 11/2009 | Kapadia et al. | |
| 7,625,392 B2 | 12/2009 | Coleman et al. | |
| 7,658,747 B2 | 2/2010 | Forde et al. | |
| 7,678,123 B2 | 3/2010 | Chanduszko | |
| 7,691,144 B2 | 4/2010 | Chang et al. | |
| 7,699,297 B2 | 4/2010 | Cicenas et al. | |
| 7,704,268 B2 | 4/2010 | Chanduszko | |
| 7,722,629 B2 | 5/2010 | Chambers | |
| 7,758,589 B2 | 7/2010 | Ortiz et al. | |
| 7,842,026 B2 | 11/2010 | Cahill et al. | |
| 7,860,579 B2 | 12/2010 | Goetzinger et al. | |
| 7,871,419 B2 | 1/2011 | Devellian et al. | |
| 7,905,901 B2 | 3/2011 | Corcoran et al. | |
| 7,967,769 B2 | 6/2011 | Faul et al. | |
| 7,976,564 B2 | 7/2011 | Blaeser et al. | |
| 8,010,186 B1 | 8/2011 | Ryu | |
| 8,021,359 B2 | 9/2011 | Auth et al. | |
| 8,034,061 B2 | 10/2011 | Amplatz et al. | |
| 8,043,360 B2 | 10/2011 | McNamara et al. | |
| 8,048,147 B2 | 11/2011 | Adams | |
| 8,052,750 B2 | 11/2011 | Tuval et al. | |
| 8,157,860 B2 | 4/2012 | McNamara et al. | |
| 8,172,896 B2 | 5/2012 | McNamara et al. | |
| 8,252,042 B2 | 8/2012 | McNamara et al. | |
| 8,303,623 B2 | 11/2012 | Melzer et al. | |
| 8,313,505 B2 | 11/2012 | Amplatz et al. | |
| 8,361,138 B2 | 1/2013 | Adams | |
| 8,398,670 B2 | 3/2013 | Amplatz et al. | |
| 8,460,372 B2 | 6/2013 | McNamara et al. | |
| 8,740,962 B2 | 6/2014 | Finch et al. | |
| 8,745,845 B2 | 6/2014 | Finch et al. | |
| 8,752,258 B2 | 6/2014 | Finch et al. | |
| 8,777,974 B2 | 7/2014 | Amplatz et al. | |
| 8,778,008 B2 | 7/2014 | Amplatz et al. | |
| 8,864,822 B2 | 10/2014 | Spence et al. | |
| 8,979,923 B2 | 3/2015 | Spence et al. | |
| 9,681,948 B2 | 6/2017 | Levi et al. | |
| 9,724,499 B2 | 8/2017 | Rottenberg et al. | |
| 2001/0027287 A1 | 10/2001 | Shmulewitz et al. | |
| 2001/0029368 A1 | 10/2001 | Berube | |

(56) References Cited

U.S. PATENT DOCUMENTS

| | | |
|---|---|---|
| 2001/0053932 A1 | 12/2001 | Phelps et al. |
| 2002/0033180 A1 | 3/2002 | Solem |
| 2002/0077698 A1 | 6/2002 | Peredo |
| 2002/0082525 A1 | 6/2002 | Oslund et al. |
| 2002/0082613 A1 | 6/2002 | Hathaway et al. |
| 2002/0095172 A1 | 7/2002 | Mazzocchi et al. |
| 2002/0120277 A1 | 8/2002 | Hauschild et al. |
| 2002/0143289 A1 | 10/2002 | Ellis et al. |
| 2002/0161424 A1 | 10/2002 | Rapacki et al. |
| 2002/0161432 A1 | 10/2002 | Mazzucco et al. |
| 2002/0165606 A1 | 11/2002 | Wolf et al. |
| 2002/0169377 A1 | 11/2002 | Khairkhahan et al. |
| 2002/0173742 A1 | 11/2002 | Keren et al. |
| 2002/0177894 A1 | 11/2002 | Acosta et al. |
| 2002/0183826 A1 | 12/2002 | Dorn et al. |
| 2003/0032967 A1 | 2/2003 | Park et al. |
| 2003/0093072 A1 | 5/2003 | Friedman |
| 2003/0125798 A1 | 7/2003 | Martin |
| 2004/0044351 A1 | 3/2004 | Searle |
| 2004/0078950 A1 | 4/2004 | Schreck |
| 2004/0087937 A1 | 5/2004 | Eggers et al. |
| 2004/0093075 A1 | 5/2004 | Kuehne |
| 2004/0102719 A1 | 5/2004 | Keith et al. |
| 2004/0102797 A1 | 5/2004 | Golden et al. |
| 2004/0111095 A1 | 6/2004 | Gordon et al. |
| 2004/0133236 A1 | 7/2004 | Chanduszko |
| 2004/0143261 A1 | 7/2004 | Hartley et al. |
| 2004/0143262 A1 | 7/2004 | Visram et al. |
| 2004/0143292 A1 | 7/2004 | Marino et al. |
| 2004/0162514 A1 | 8/2004 | Alferness et al. |
| 2004/0176788 A1 | 9/2004 | Opolski |
| 2004/0193261 A1 | 9/2004 | Berreklouw |
| 2004/0206363 A1 | 10/2004 | McCarthy et al. |
| 2004/0220653 A1 | 11/2004 | Borg et al. |
| 2004/0236308 A1 | 11/2004 | Herweck et al. |
| 2004/0243143 A1 | 12/2004 | Corcoran et al. |
| 2004/0267306 A1 | 12/2004 | Blaeser et al. |
| 2005/0015953 A1 | 1/2005 | Keidar |
| 2005/0049692 A1 | 3/2005 | Numamoto et al. |
| 2005/0049697 A1 | 3/2005 | Sievers |
| 2005/0065507 A1 | 3/2005 | Hartley et al. |
| 2005/0065546 A1 | 3/2005 | Corcoran et al. |
| 2005/0065548 A1 | 3/2005 | Marino et al. |
| 2005/0070934 A1 | 3/2005 | Tanaka et al. |
| 2005/0075655 A1 | 4/2005 | Bumbalough et al. |
| 2005/0075665 A1 | 4/2005 | Brenzei et al. |
| 2005/0080400 A1 | 4/2005 | Corcoran et al. |
| 2005/0080430 A1 | 4/2005 | Wright et al. |
| 2005/0096735 A1 | 5/2005 | Hojeibane et al. |
| 2005/0113868 A1 | 5/2005 | Devellian et al. |
| 2005/0131503 A1 | 6/2005 | Salem |
| 2005/0137609 A1 | 6/2005 | Guiraudon |
| 2005/0137686 A1 | 6/2005 | Salahieh et al. |
| 2005/0148925 A1* | 7/2005 | Rottenberg ...... A61B 17/00234 604/9 |
| 2005/0159738 A1 | 7/2005 | Visram et al. |
| 2005/0165344 A1 | 7/2005 | Dobak |
| 2005/0187616 A1 | 8/2005 | Realyvasquez |
| 2005/0234537 A1 | 10/2005 | Edin |
| 2005/0240205 A1 | 10/2005 | Berg et al. |
| 2005/0251063 A1 | 11/2005 | Basude |
| 2005/0251187 A1 | 11/2005 | Beane et al. |
| 2005/0267524 A1 | 12/2005 | Chanduszko |
| 2005/0273075 A1 | 12/2005 | Krulevitch et al. |
| 2005/0273124 A1 | 12/2005 | Chanduszko |
| 2005/0288722 A1 | 12/2005 | Eigler et al. |
| 2006/0004323 A1 | 1/2006 | Chang et al. |
| 2006/0009800 A1 | 1/2006 | Christianson et al. |
| 2006/0009832 A1 | 1/2006 | Fisher |
| 2006/0041183 A1 | 2/2006 | Massen et al. |
| 2006/0085060 A1 | 4/2006 | Campbell |
| 2006/0095066 A1 | 5/2006 | Chang et al. |
| 2006/0111704 A1 | 5/2006 | Brenneman et al. |
| 2006/0122646 A1 | 6/2006 | Corcoran et al. |
| 2006/0122647 A1 | 6/2006 | Callaghan et al. |
| 2006/0135990 A1 | 6/2006 | Johnson |
| 2006/0136043 A1 | 6/2006 | Cully et al. |
| 2006/0155305 A1 | 7/2006 | Freudenthal et al. |
| 2006/0184088 A1 | 8/2006 | Van Bibber et al. |
| 2006/0210605 A1 | 9/2006 | Chang et al. |
| 2006/0217761 A1 | 9/2006 | Opolski |
| 2006/0224183 A1 | 10/2006 | Freudenthal |
| 2006/0241675 A1 | 10/2006 | Johnson et al. |
| 2006/0241745 A1* | 10/2006 | Solem ................. A61F 2/246 623/2.18 |
| 2006/0247680 A1 | 11/2006 | Amplatz et al. |
| 2006/0253184 A1 | 11/2006 | Amplatz |
| 2006/0259121 A1 | 11/2006 | Osypka |
| 2006/0276882 A1 | 12/2006 | Case et al. |
| 2007/0005127 A1 | 1/2007 | Boekstegers et al. |
| 2007/0010851 A1 | 1/2007 | Chanduszko et al. |
| 2007/0021739 A1 | 1/2007 | Weber |
| 2007/0027528 A1 | 2/2007 | Agnew |
| 2007/0038295 A1 | 2/2007 | Case et al. |
| 2007/0043431 A1 | 2/2007 | Melsheimer |
| 2007/0088375 A1 | 4/2007 | Beane et al. |
| 2007/0088388 A1 | 4/2007 | Opolski et al. |
| 2007/0118207 A1 | 5/2007 | Amplatz et al. |
| 2007/0123934 A1 | 5/2007 | Whisenant et al. |
| 2007/0129755 A1 | 6/2007 | Abbott et al. |
| 2007/0168018 A1 | 7/2007 | Amplatz et al. |
| 2007/0185513 A1 | 8/2007 | Woolfson et al. |
| 2007/0197952 A1 | 8/2007 | Stiger |
| 2007/0198060 A1 | 8/2007 | Devellian et al. |
| 2007/0209957 A1 | 9/2007 | Glenn et al. |
| 2007/0225759 A1 | 9/2007 | Thommen et al. |
| 2007/0265658 A1 | 11/2007 | Nelson et al. |
| 2007/0270741 A1 | 11/2007 | Hassett et al. |
| 2007/0282157 A1 | 12/2007 | Rottenberg et al. |
| 2008/0015619 A1 | 1/2008 | Figulla et al. |
| 2008/0033425 A1 | 2/2008 | Davis et al. |
| 2008/0033543 A1 | 2/2008 | Gurskis et al. |
| 2008/0039804 A1 | 2/2008 | Edmiston et al. |
| 2008/0039881 A1 | 2/2008 | Greenberg |
| 2008/0039922 A1 | 2/2008 | Miles et al. |
| 2008/0058940 A1 | 3/2008 | Wu et al. |
| 2008/0071135 A1 | 3/2008 | Shaknovich |
| 2008/0086168 A1 | 4/2008 | Cahill |
| 2008/0103508 A1 | 5/2008 | Karakurum |
| 2008/0109069 A1 | 5/2008 | Coleman et al. |
| 2008/0119891 A1 | 5/2008 | Miles et al. |
| 2008/0125861 A1 | 5/2008 | Webler et al. |
| 2008/0154250 A1 | 6/2008 | Makower et al. |
| 2008/0154302 A1 | 6/2008 | Opolski et al. |
| 2008/0154351 A1 | 6/2008 | Leewood et al. |
| 2008/0154355 A1 | 6/2008 | Benichou et al. |
| 2008/0161901 A1 | 7/2008 | Heuser et al. |
| 2008/0172123 A1 | 7/2008 | Yadin |
| 2008/0177381 A1 | 7/2008 | Navia et al. |
| 2008/0183279 A1 | 7/2008 | Bailey et al. |
| 2008/0188880 A1 | 8/2008 | Fischer et al. |
| 2008/0188888 A1 | 8/2008 | Adams et al. |
| 2008/0215008 A1 | 9/2008 | Nance et al. |
| 2008/0221582 A1 | 9/2008 | Gia et al. |
| 2008/0228264 A1 | 9/2008 | Li et al. |
| 2008/0249397 A1 | 10/2008 | Kapadia |
| 2008/0249612 A1 | 10/2008 | Osborne et al. |
| 2008/0262592 A1 | 10/2008 | Jordan et al. |
| 2008/0269662 A1 | 10/2008 | Vassiliades et al. |
| 2008/0312679 A1 | 12/2008 | Hardert et al. |
| 2009/0018570 A1 | 1/2009 | Righini et al. |
| 2009/0030495 A1 | 1/2009 | Koch |
| 2009/0054805 A1 | 2/2009 | Boyle |
| 2009/0054982 A1 | 2/2009 | Cimino |
| 2009/0054984 A1 | 2/2009 | Shortkroff et al. |
| 2009/0062841 A1 | 3/2009 | Amplatz et al. |
| 2009/0076541 A1 | 3/2009 | Chin et al. |
| 2009/0082803 A1 | 3/2009 | Adams et al. |
| 2009/0099647 A1 | 4/2009 | Glimsdale et al. |

(56) References Cited

U.S. PATENT DOCUMENTS

| | | |
|---|---|---|
| 2009/0112050 A1 | 4/2009 | Farnan et al. |
| 2009/0112244 A1 | 4/2009 | Freudenthal |
| 2009/0112251 A1 | 4/2009 | Qian et al. |
| 2009/0177269 A1 | 7/2009 | Kalmann et al. |
| 2009/0234443 A1 | 9/2009 | Ottma et al. |
| 2010/0030259 A1 | 2/2010 | Pavcnik et al. |
| 2010/0057192 A1 | 3/2010 | Celermajer |
| 2010/0114140 A1 | 5/2010 | Chanduszko |
| 2010/0131053 A1 | 5/2010 | Agnew |
| 2010/0268316 A1 | 10/2010 | Brenneman et al. |
| 2010/0298755 A1 | 11/2010 | McNamara et al. |
| 2011/0004296 A1 | 1/2011 | Lutter et al. |
| 2011/0040374 A1 | 2/2011 | Goetz et al. |
| 2011/0071623 A1 | 3/2011 | Finch et al. |
| 2011/0071624 A1 | 3/2011 | Finch et al. |
| 2011/0106149 A1 | 5/2011 | Ryan et al. |
| 2011/0130784 A1 | 6/2011 | Kusleika |
| 2011/0190874 A1 | 8/2011 | Celermajer et al. |
| 2011/0213364 A1 | 9/2011 | Davis et al. |
| 2011/0218479 A1 | 9/2011 | Rottenberg et al. |
| 2011/0257723 A1 | 10/2011 | McNamara |
| 2011/0295183 A1 | 12/2011 | Finch et al. |
| 2012/0130301 A1 | 5/2012 | McNamara et al. |
| 2012/0259263 A1 | 10/2012 | Celermajer et al. |
| 2012/0265296 A1 | 10/2012 | McNamara et al. |
| 2012/0289882 A1 | 11/2012 | McNamara et al. |
| 2012/0290062 A1 | 11/2012 | McNamara et al. |
| 2013/0178783 A1 | 7/2013 | McNamara et al. |
| 2013/0178784 A1 | 7/2013 | McNamara et al. |
| 2013/0184633 A1 | 7/2013 | McNamara et al. |
| 2013/0184634 A1 | 7/2013 | McNamara et al. |
| 2013/0204175 A1 | 8/2013 | Sugimoto |
| 2013/0231737 A1 | 9/2013 | McNamara et al. |
| 2013/0267885 A1 | 10/2013 | Celermajer et al. |
| 2014/0012368 A1 | 1/2014 | Sugimoto et al. |
| 2014/0194971 A1 | 7/2014 | McNamara |
| 2014/0277054 A1 | 9/2014 | McNamara et al. |
| 2015/0039084 A1 | 2/2015 | Levi et al. |
| 2015/0119796 A1 | 4/2015 | Finch |
| 2016/0051800 A1 | 2/2016 | Vassiliades et al. |
| 2016/0166381 A1 | 6/2016 | Sugimoto et al. |
| 2017/0128705 A1 | 5/2017 | Forcucci et al. |

FOREIGN PATENT DOCUMENTS

| | | |
|---|---|---|
| CN | 1582136 A | 2/2005 |
| CN | 1780589 A | 5/2006 |
| CN | 101035481 A | 9/2007 |
| CN | 101035488 A | 9/2007 |
| CN | 101292889 A | 10/2008 |
| CN | 101426431 A | 5/2009 |
| EP | 1264582 A2 | 2/2002 |
| EP | 1480565 A1 | 9/2003 |
| EP | 1470785 A1 | 10/2004 |
| EP | 1849440 A1 | 10/2007 |
| FR | 2827153 A1 | 1/2003 |
| JP | 58-27935 U | 6/1983 |
| JP | H02-277459 A | 11/1990 |
| JP | 2003530143 | 10/2003 |
| WO | WO95/27448 A1 | 10/1995 |
| WO | WO98/08456 A1 | 3/1998 |
| WO | WO98/42403 A1 | 10/1998 |
| WO | WO01/15618 A2 | 3/2001 |
| WO | WO02/094363 A2 | 11/2002 |
| WO | WO2004/019811 A2 | 3/2004 |
| WO | WO2005/048881 A1 | 6/2005 |
| WO | WO2005/048883 A1 | 6/2005 |
| WO | WO2006/127765 A1 | 11/2006 |
| WO | WO2007/054116 A | 5/2007 |
| WO | WO2007/083288 A2 | 7/2007 |
| WO | WO2008/058940 A1 | 5/2008 |

OTHER PUBLICATIONS

Atz et al.; Preoperative management of pulmonary venous hypertension in hypoplastic left heart syndrome with restrictive atrial septal defect; the American Journal of Cardiology; 83; pp. 1224-1228; Apr. 15, 1999.

Bailey, Steven R.; Nanotechnology in prosthetic heart valves (presentation); 31 pgs.; 2005 (year of pub. sufficiently earlier than effective US filing date and any foreign priority date).

Cheatham, John P.; Intervention in the critically ill neonate and infant with hypoplastic left heart syndrome and intact atrial septum; Journal of Interventional Cardiology; 14(3); pp. 357-366; Jun. 2001.

Coselli, Joseph S.; No! Valve replacement: Patient prosthetic mismatch rarely occurs (presentation); 75 pgs.; Apr. 25, 2009.

Design News; Low power piezo motion; retrieved from the internet (http://www.designnews.com/document.asp?doc_id=229053&dfpPParams=ht_13,aid_229053&dfpLayout=article); 3 pgs.; May 14, 2010.

Hijazi, Zayad M.; Valve implantation (presentation); 36 pgs.; May 10, 2007.

Larios et al.; The use of an artificial foraminal valve prosthesis in the closure of interatrial and interventricular septal defects; Chest; 36(6); pp. 631-641; Dec. 1959.

O'Loughlin et al.; Insertion of a fenestrated amplatzer atrial sestostomy device for severe pulmonary hypertension; Heart Lung Circ.; 15(4); pp. 275-277; Aug. 2006.

Park et al.; Blade atrial septostomy: Collaborative study; Circulation; 66(2); pp. 258-266; Aug. 1982.

Pedra et al.; Stent implantation to create interatrial communications in patients with complex congenital heart disease; Catheterization and Cardiovascular Interventions; 47; pp. 310-313; Jan. 27, 1999.

Perry et al.; Creation and maintenance of an adequate interatrial communication in left atrioventricular valve atresia or stenosis; The American Journal of Cardiology; 58; pp. 622-626; Sep. 15, 1986.

Philips et al.; Ventriculofemoroatrial shunt: A viable alternative for the treatment of hydrocephalus; J. Neurosurg.; 86; pp. 1063-1066; Jun. 1997.

Physik Instrumente; Piezo for Motion Control in Medical Design and Drug Research (product information); Physik Instrumente (PI) GmbH & Co. KG; 22 pgs.; ©Nov. 21, 2010.

Roven et al.; Effect of compromising right ventricular function in left ventricular failure by means of interatrial and other shunts; Am J Cardiol.; 24(2); pp. 209-219; Aug. 1969.

Sambhi et al.; Pathologic Physiology of Lutembacher Syndrome; Am J Cardiol.; 2(6); pp. 681-686; Dec. 1958.

Sommer et al.; Transcatheter creation of atrial septal defect and fontan fenestration with "butterfly" stent technique; Journal of the American college of Cardiology; 33(2); Suppl. A; 3 pgs.; Feb. 1999.

Stormer et al.; Comparative study of in vitro flow characteristics between a human aortic valve and a designed aortic valve and six corresponding types of prosthetic heart valves; Eur Surg Res; 8(2); pp. 117-131; 1976 (year of pub. sufficiently earlier than effective US filed and any foreign priority date).

Watterson et al.; Very small pulmonary arteries: Central end-to-side shunt; Ann. Thorac. Surg.; 52(5); pp. 1132-1137; Nov. 1991.

Celermajer et al.; U.S. Appl. No. 14/498,903 entitled "Apparatus and methods to create and maintain an intra-atrial pressure relief opening," filed Sep. 26, 2014.

Mcnamara et al.; U.S. Appl. No. 14/612,022 entitled "Methods and devices for intra-atrial shunts having adjustable sizes," filed Feb. 2, 2015.

Forcucci et al.; U.S. Appl. No. 14/807,544 entitled "Devices and methods for treating heart failure," filed Jul. 23, 2015.

Finch; U.S. Appl. No. 14/645,416 entitled "Devices and methods for treating heart failure," filed Mar. 11, 2015.

McNamara et al.; U.S. Appl. No. 14/878,710 entitled "Methods, systems, and devices for resizable intra-atrial shunts," filed Oct. 8, 2015.

* cited by examiner

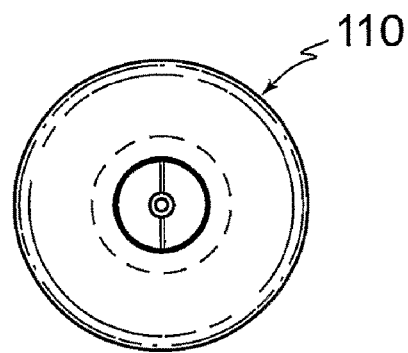
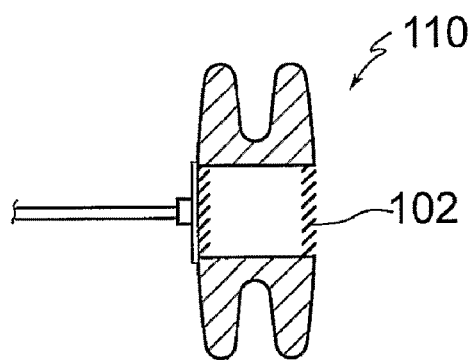
Figure 19a  Figure 19b
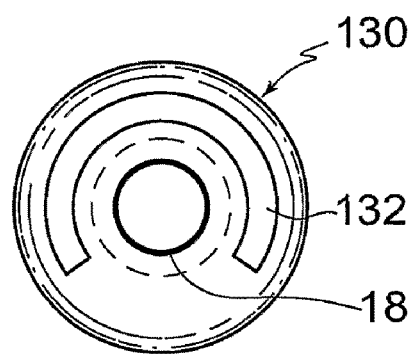
Figure 20

DEVICES AND METHODS FOR THE TREATMENT OF HEART FAILURE

CROSS REFERENCE TO RELATED APPLICATIONS

This application is a continuation of pending U.S. application Ser. No. 12/447,617, filed Apr. 28, 2009, which is the national phase filing of International Application No. PCT/AU2007/001704, filed Nov. 7, 2007, which application claims priority to Australian Application. No. 2006906202, filed Nov. 7, 2006.

FIELD OF THE INVENTION

The present invention relates generally to devices and methods for the treatment of heart failure and, more particularly, to devices and methods for the relief of high pressure in the cardiovascular system to alleviate symptoms of cardiovascular disease.

BACKGROUND OF THE INVENTION

Heart failure is a common and potentially lethal condition affecting humans, with sub-optimal clinical outcomes often resulting in symptoms, morbidity and/or mortality, despite maximal medical treatment. In particular, "diastolic heart failure" refers to the clinical syndrome of heart failure occurring in the context of preserved left ventricular systolic function (ejection fraction) and in the absence of major valvular disease. This condition is characterised by a stiff left ventricle with decreased compliance and impaired relaxation, which leads to increased end-diastolic pressure. Approximately one third of patients with heart failure have diastolic heart failure and there are very few, if any, proven effective treatments.

Symptoms of diastolic heart failure are due, at least in a large part, to an elevation in pressure in the left atrium. In addition to diastolic heart failure, a number of other medical conditions, including systolic dysfunction of the left ventricle and valve disease, can lead to elevated pressures in the left atrium. Increased left atrial pressure often causes acute or chronic breathlessness amongst other problems. In addition, a variety of heart conditions can lead to "right heart failure", which can result in enlargement of the liver (hepatomegaly), fluid accumulation in the abdomen (ascites) and/or swelling of the lower limbs.

In the past, strategies have been described for the relief of high pressure in the right atrium, such as the creation of hole(s) in the native or surgically created septum between the left and right atria. These have been designed for the rare conditions of pulmonary hypertension or cavopulmonary connections for certain complex congenital heart diseases. O'Loughlin et al. recently described a fenestrated atrial septal defect closure device for the palliation of advanced pulmonary hypertension. However, this device allows bidirectional flow, and the passage of thrombi, and was shown to be closed over within 6 months of insertion. Thus a need still exists for devices to relieve high pressure in the left atrium and which will prevent or minimize the chance of the passage of thrombi.

Accordingly, there exists a need for devices and methods to treat heart failure particularly diastolic and/or systolic failure of the left ventricle and its consequences.

SUMMARY OF THE INVENTION

According to a first aspect of the invention, there is provided a device for treating heart failure in a patient, the device comprising:

a body;
at least one passage through the body;
at least one one way valve in the passage; and
a mounting means adapted for mounting the body in an opening provided in the patient's atrial septum,
wherein, in use, the device is oriented such that, when the patient's left atrial pressure exceeds the patient's right atrial pressure by a predetermined amount, the one way valve(s) opens to allow blood flow through the passage(s) from the left atrium to the right atrium to thereby reduce the left atrial pressure.

According to a second aspect of the invention, there is provided a device for treating heart failure or pulmonary venous hypertension in a patient, the device comprising:

a body;
at least one passage through the body;
at least one one way valve in the passage; and
a mounting means adapted for mounting the body in the patient's venous system,
wherein, in use, the device is oriented such that the one way valve(s) prevents blood flow through the passage(s) in a direction opposite to that of the natural flow direction.

The device is preferably adapted to be fitted into a blood vessel in the patient's venous system, such as the inferior vena cava, superior vena cava, the hepatic vein, an iliac vein, or one or more pulmonary veins.

According to a third aspect of the invention, there is provided a device for treating lower limb venous hypertension in a patient, the device comprising:

a body;
at least one passage through the body;
at least one one way valve in the passage; and
a mounting means adapted for mounting the body in the patient's lower limb venous system,
wherein, in use, the device is oriented such that the one way valve(s) prevents blood flow through the passage(s) in a direction opposite to that of the natural flow direction.

The above device is also suitable for treating varicose veins.

The body is preferably in the form of a stent, most preferably an expandable stent.

The valve is preferably a duckbill valve, a leaflet valve, a flap valve, a disc in cage type valve or a ball in cage type valve. The valve is preferably biased to a closed position, most preferably by the inherent resilience of the valve material. The valve preferably opens when the predetermined amount of pressure differential is at least approximately 2 mm Hg, preferably approximately 5 to 25 mm Hg, even more preferably 5 to 15 mm Hg.

In one form, the device has a single passage through the body, most preferably centrally located in relation to the body. In another form, the device has a single passage through the body, most preferably eccentrically located in relation to the body. In yet another form, the device has a plurality of passages through the body, each with a one way valve therein, most preferably each eccentrically located in relation to centre of the body.

According to a fourth aspect of the invention, there is provided a device for treating heart failure in a patient, the device comprising:

a body;
at least one passage through the body;
a mesh or grill arrangement within the passage and having apertures therein of a size permitting flow of blood, whilst substantially excluding thrombi, therethrough;
a mounting means adapted for mounting the body in an opening provided in the patient's atrial septum, wherein, in use, the device allows blood flow through the passage(s) from the left atrium to the right atrium when the patient's left atrial pressure exceeds the patient's right atrial pressure to thereby reduce the patient's left atrial pressure.

The device preferably includes a mesh or grill arrangement across one or both ends of the passage(s).

The apertures preferably have a maximum dimension of less than 4 mm, most preferably less than 2 mm. The mesh or grill is preferably coated or impregnated with one or more drugs, adapted for preventing thrombosis or endothelialisation of the opening in the patient's atrial septum, including an anticoagulant substance, such as heparin, or an inhibitor of re-endothelialisation, such as sirolimus or paclitaxel.

In one form, the device has a single passage through the body, most preferably centrally located in relation to the body. In another form, the device has a plurality of passages through the body, each with a mesh or grill arrangement therein, most preferably each eccentrically located in relation to centre of the body.

The device is preferably flexible, most preferably formed from a material which can be deformed but later return to its original shape. An example of such a material is Nitinol.

The device is preferably collapsible and adapted for implanting via a catheter, although it could be inserted at surgery.

The device is preferably collapsible to a size able to pass through an opening made in the patient's atrial septum (or an enlargement of a pre-existing communication, by standard methods) and adapted to return to a shape where at least some of the device would have been unable to pass through the opening in the patient's atrial septum. The device is preferably formed from a Nitinol mesh, or any other material which can be deformed but later return to its original shape.

The mounting means preferably comprises at least one flange having a dimension larger than the opening in the patient's septum. More preferably, the mounting means preferably comprises a pair of spaced apart flanges having a dimension larger than the opening in the patient's septum.

The external dimension of the body, remote the flange(s), is preferably substantially equal to the opening in the patient's atrial septum.

In one embodiment, the flanges are adapted for gluing, suturing, stapling or pinning to the patient's septum.

In another embodiment, the flanges are spaced apart by about the thickness of the patient's atrial septum and are adapted to locate, most preferably by gripping, the patient's atrial septum therebetween.

According to a fifth aspect of the invention, there is provided a method for treating heart failure in a patient, the method comprising the steps of:

forming an opening in the patient's atrial septum;

inserting at least one one way valve in the opening that is oriented such that the one way valve(s) allows blood flow through the passage from the left atrium to the right atrium when the patient's left atrial pressure exceeds the patient's right atrial pressure; and securing the one way valve(s) relative to the patient's atrial septum, whereby, when the patient's left atrial pressure exceeds the patient's right atrial pressure by a predetermined amount, the valve opens to allow blood flow through the passage(s) from the left atrium to the right atrium to thereby reduce the patient's left atrial pressure.

The above method is particularly suited for treating cardiovascular disease manifest by left atrial hypertension, such as that due to left ventricular systolic or diastolic dysfunction.

The predetermined amount of pressure differential is at preferably least approximately 3 mm Hg, preferably approximately 5 to 25 mm Hg, even more preferably 5 to 15 mm Hg.

According to a sixth aspect of the invention, there is provided a method for treating heart failure in a patient, the method comprising the steps of:

forming an opening in the patient's atrial septum;

inserting a mesh or grill arrangement within the opening having apertures therein of a size permitting passage of blood, whilst substantially excluding passage of thrombi, therethrough; and securing the mesh or grill arrangement relative to the patient's atrial septum.

The mesh or grill arrangement is preferably provided within a passage in a body, and the method preferably includes the step of securing the body relative to the patient's atrial septum.

The above method is particularly suited for treating cardiovascular disease manifest by left atrial hypertension, such as that due to left ventricular systolic or diastolic dysfunction.

According to a seventh aspect of the invention, there is provided a method for treating heart failure in a patient, the method comprising the steps of:

inserting at least one one way valve in the patient's venous system that is oriented such that the one way valve(s) prevents blood flow through the said venous system in a direction opposite to that of the natural flow direction; and securing the one way valve(s) relative to the patient's venous system.

The method preferably includes the steps of inserting and securing the one way valve in the patient's blood vessel, such as the inferior vena cava, superior vena cava, the hepatic vein, an iliac vein, or one or more pulmonary veins.

The method preferably includes a step of inserting and securing, most preferably by expanding, a stent with the one way valve(s) therein.

According to an eighth aspect of the invention, there is provided a device for treating heart failure in a patient, the device comprising:

a tube having first and second ends in fluid communication with the left and right atriums of the heart respectively; and a valve between the first and second ends and adapted to selectively prevent or allow fluid flow through the tube, wherein, in use, when the patient's left atrial pressure exceeds the patient's right atrial pressure by a predetermined amount, the valve opens to allow blood flow through the tube from the left atrium to the right atrium to thereby reduce the left atrial pressure.

The valve opens when the predetermined amount of pressure differential is at preferably least approximately 2 mm Hg, preferably approximately 5 to 25 mm Hg, even more preferably approximately 5 to 15 mm Hg.

According to an ninth aspect of the invention, there is provided a device for treating heart failure or pulmonary venous hypertension in a patient, the device comprising:

a tube having first and second ends in fluid communication with the left and right atriums of the heart respectively; and a one way valve in the tube, wherein, in use, the one way valve prevents blood flow through the tube from the right atrium to the left atrium.

According to a tenth aspect of the invention, there is provided a method for treating heart failure in a patient, the method comprising the steps of:

connecting a tube externally between the patient's left and right atriums; and inserting a one way valve in the tube that is oriented such that the one way valve allows blood flow through the passage from the left atrium to the right atrium when the patient's left atrial pressure exceeds the patient's right atrial pressure, whereby, when the patient's left atrial pressure exceeds the patient's right atrial pressure, by a predetermined amount, the valve open to allow blood flow through the passage(s) from the left atrium to the right atrium to thereby reduce the patient's left atrial pressure.

The predetermined amount of pressure differential is at preferably least approximately 2 mm Hg, preferably approximately 5 to 25 mm Hg, even more preferably approximately 5 to 15 mm Hg.

BRIEF DESCRIPTION OF THE DRAWINGS

Preferred embodiments of the invention will now be described, by way of examples only, with reference to the accompanying drawings in which:

FIG. 19a is a front view of a ninth embodiment of a device for treating heart failure;

FIG. 19b is a cross sectional side view the device shown in FIG. 19a;

FIG. 20 is a front view of a tenth embodiment of a device for treating heart failure.

DETAILED DESCRIPTION OF THE PREFERRED EMBODIMENTS

Figure 1:
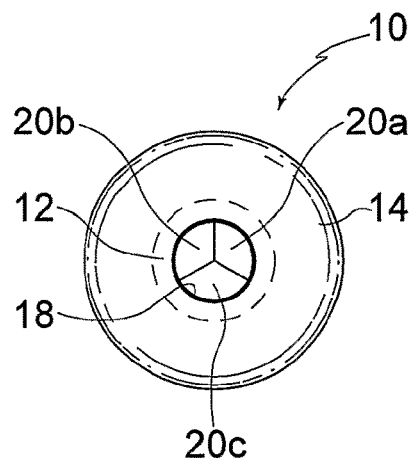
FIG. 1 is a front view of a first embodiment of a device for treating heart failure.
Figure 2:
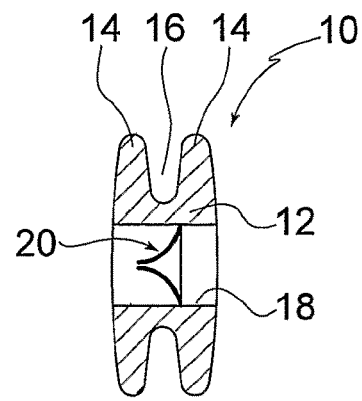
FIG. 2 is a cross sectional side view of the device shown in FIG. 1.

FIGS. 1 to 4 show a first embodiment of a device 10 for treating heart failure. The device 10 includes a generally cylindrical body 12 with a mounting means, in the form of a pair of annular flanges 14 at either end with an annular gap 16 therebetween. The body 12 has a centrally located passage or duct 18 within which is provided a one way valve 20, in the form of three flexible valve leaflets 20a to 20c.

The external diameters of the body 12, the flanges 14 and internal diameter of the passage 18 are approximately 18, 38 and 12 mm respectively. In other embodiments (not shown), the diameter of the body 12 ranges from 8 to 25 mm, the diameter of the flanges 14 ranges from 20 to 50 mm, and the diameter of the passage 18 ranges from 4 to 15 mm.

Figure 3:
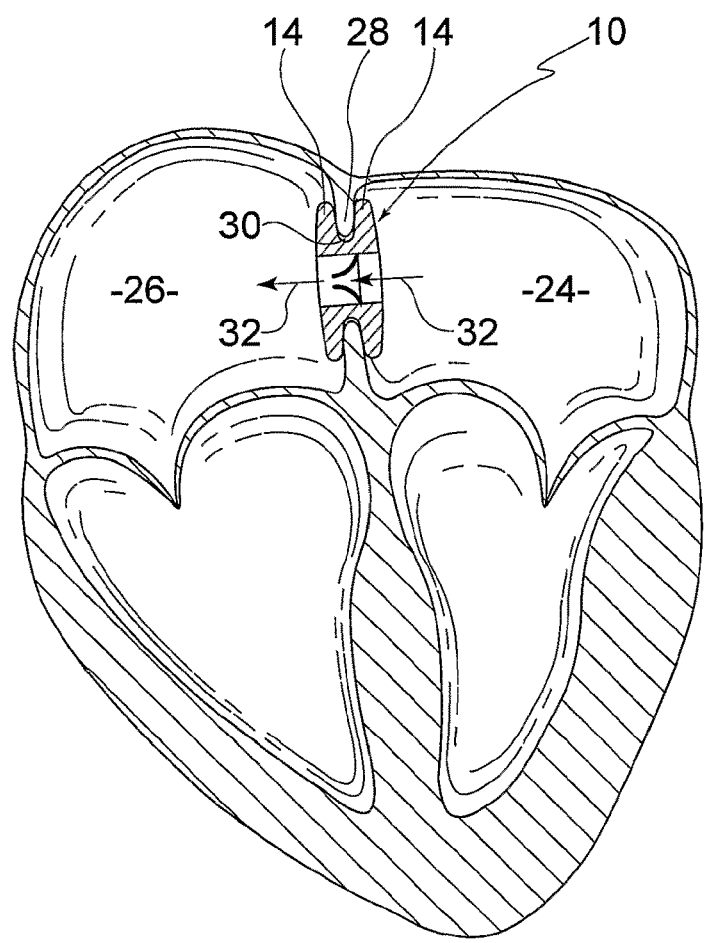
FIG. 3 is a cross sectional side view of the device shown in FIGS. 1 and 2 implanted in a human heart.

FIG. 3 shows a patient's heart 22 with a left atrium 24 and a right atrium 26 separated by an atrial septum 28. The device 10 is mounted within a generally circular opening 30 made in the septum 28 and with the edges of the septum 28 adjacent the opening 30 positioned in the gap 16 between the flanges 14. The opening 30 has an internal diameter approximately equal to the external diameter of the body 12. The device 10 is retained adjacent the opening 30 in the septum 28 as the flanges 14 are larger, and thus cannot pass through, the opening 30. Alternatively, or in addition, one or both of the flanges 14 can be glued, sutured, stapled or pinned to the patient's septum 28 to secure the device 10 thereto.

The device 10 can be implanted during open heart surgery or percutaneously using a catheter. In either case, the opening 30 is firstly fashioned in the patient's atrial septum 28. Some or all of the device 10 is then collapsed to a size able to pass through the opening 30 and subsequently expanded to the configuration shown in FIG. 3. Forming the s body 12 and the flanges 14 of the device 10 from a Nitinol wire mesh result in it being suitable for implanting in a manner similar to the implanting of the AMPLATZER (Trade Mark) septal occluder produced by AGA Medical Corp. More particularly, the exterior faces of the flanges 14 are pulled away from one another which causes the device 10 to lengthen and simultaneously reduce in diameter for fitting within a catheter able to pass through the opening 30. When the separating force is then removed the flanges 14 return to the (expanded) configuration in FIGS. 1 to 4.

The device 10 is orientated during implanting with the one way valve 20 only allowing blood flow through the passage 18 from the left atrium 24 to the right atrium 26, as indicated by arrows 32. More particularly, when the left atrial pressure exceeds the right atrial pressure by about 5-15 mm Hg, the valve leaflets 20a to c separate and thus open the passage 18 to blood flow from the left atrium 24 to the right atrium 26.

The leaflets 20a to 20c are formed from biological, mechanical or engineered tissue and are inherently biased towards a closed position. Further, the patient's right atrial pressure exceeding the left atrial pressure also assists in the closing, and the maintaining closed, of the valve 20.

The relief and/or avoidance of the left atrial pressure significantly exceeding the right atrial pressure is beneficial in alleviating the adverse consequences of left atrial hypertension complicating cardiovascular diseases, including left ventricular systolic and/or diastolic dysfunction and/or valvular diseases.

Figure 4:
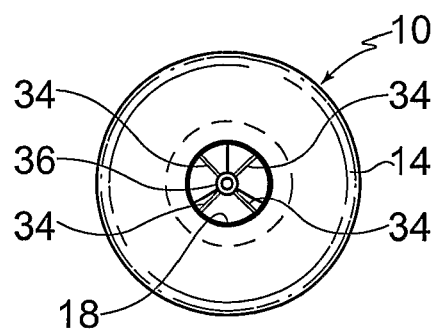
FIG. 4 is a rear view of the device shown in FIG. 1.

As best seen in FIG. 4, the device 10 includes four thin collapsible struts 34 connected to a central fixture or boss 36 having an internally threaded opening. A cable (not shown) is threadedly attachable to the fixture 36. The fixture 36 is accessible from the left atrium.

To implant the device 10, it is firstly collapsed inside a catheter. When the catheter is correctly positioned adjacent the opening 30, the cable is used to push the device 10 out of the catheter, whereafter it expands to the shape shown in FIG. 3. The cable is then unscrewed from the fixture 36 and removed from the patient with the catheter.

The device 10 can also be adapted to allow later removal by a percutaneous route, for example by the placement of small hooks (not shown) on a surface of the device 10 that is closest to a nearby venous access site.

Figure 5:
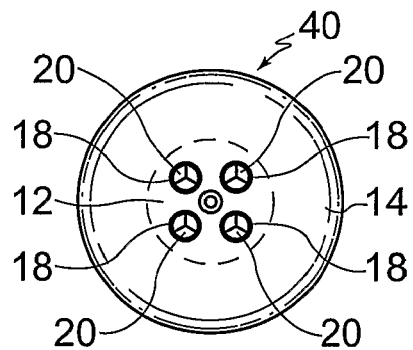
FIG. 5 is a front view of a second embodiment of a device for treating heart failure.

FIG. 5 shows a second embodiment of a device 40 for treating heart failure. The construction, function and implanting of the device 40 is similar to that of the device 10 and like reference numerals are used to indicate like features between the two embodiments. However, the device 40 has four eccentrically located passages 18 through the body 12 and blood flow therethrough is controlled by four corresponding sets of valve leaflets 20.

Figure 6:
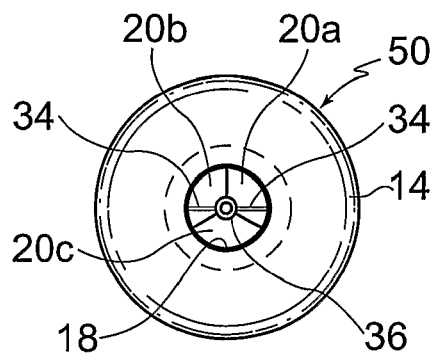
FIG. 6 is a front view of a third embodiment of a device to treat heart failure.
Figure 7:
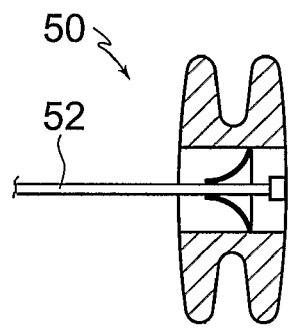
FIG. 7 is a cross sectional side view of the device shown in FIG. 6.

FIGS. 6 and 7 show a third embodiment of a device 50 for treating heart failure. The construction, operation and implantation of the device 50 is similar to that of the device 10 and like reference numerals are used to indicate like features between the two embodiments. However, the device 50 has only one collapsible strut 34 connected to a central fixture 36, to which a cable 52 can be attached. The fixture 36 is also accessible from the left atrium. In a variation of this embodiment, the fixture is accessible from the right atrium.

Figure 8:
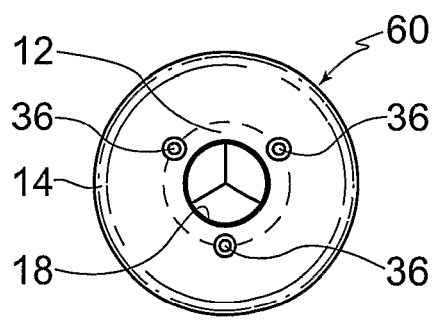
FIG. 8 is a front view of a fourth embodiment of a device to treat heart failure.
Figure 9:
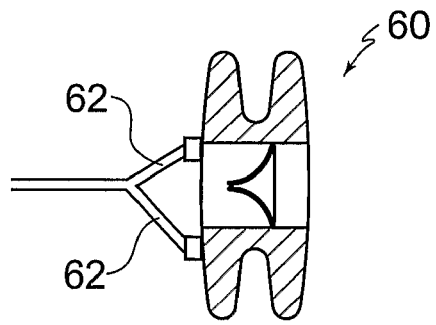
FIG. 9 is a cross sectional side view of the device shown in FIG. 8.

FIGS. 8 and 9 show a fourth embodiment of a device 60 for treating heart failure. The construction, function and implanting of the device 60 is similar to that of the device 10 and like reference numerals are used to indicate like features between the two embodiments. However, the device 60 has three fixtures 36 attached to the body 12, adjacent the passage 18, to which three respective cables 62 (see FIG. 9) can be attached. The fixtures 36 are accessible from the right atrium.

Figure 10:
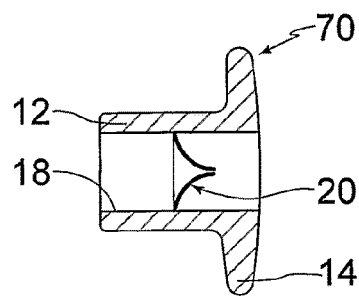
FIG. 10 is a cross sectional side view of a fifth embodiment of a device for treating heart failure.
Figure 11:
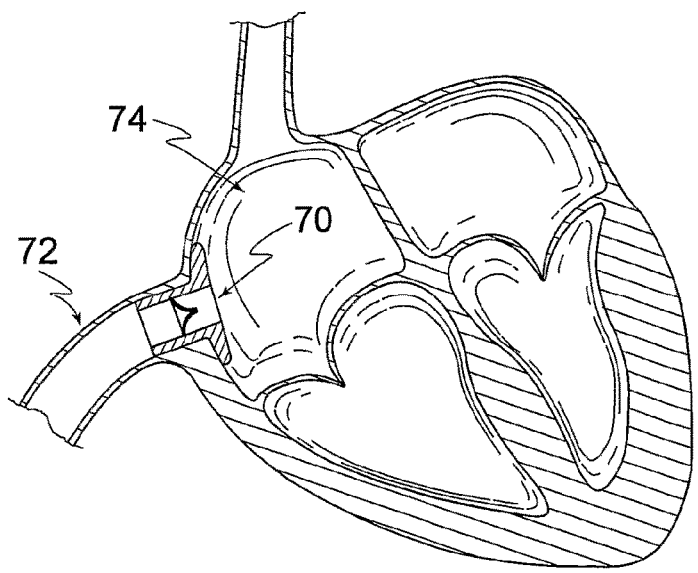
FIG. 11 is a cross sectional side view of the device shown in FIG. 10 implanted in a patient's inferior vena cava.

FIGS. 10 and 11 show a fifth embodiment of a device 70 for treating heart failure, in a manner similar to that of the device 10. However, unlike the earlier embodiments, the device 70 only has a single mounting flange 14 which, as shown in FIG. 11, makes it suitable for implanting in the inferior vena cava 72 at or near the junction with the right atrium 74. The device 70 is preferably produced from a deformable material that can resume its preformed shape (such as Nitinol) and may be implanted by a percutaneous approach.

More particularly, the device 70 is collapsed and introduced in the venous system within a sheath, and removed from the sheath to expand when correctly positioned.

Figure 12:
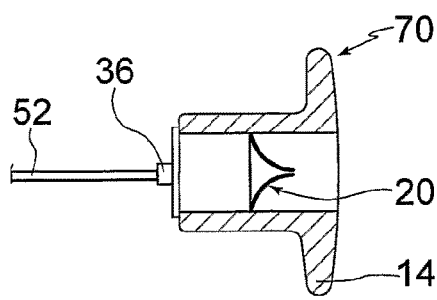
FIG. 12 is a cross sectional side view of a first embodiment of a delivery mechanism for the device shown in FIG. 10.
Figure 13:
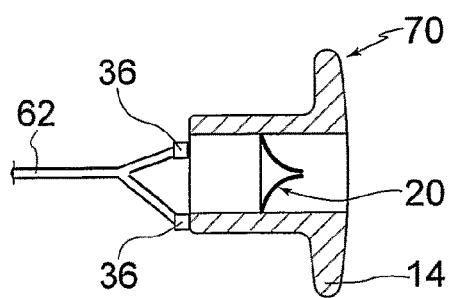
FIG. 13 is a cross sectional side view of a second embodiment of a delivery mechanism for the device shown in FIG. 10.

FIGS. 12 and 13 show two mechanisms suitable for delivering the device 70 to the inferior vena cava. The mechanism shown in FIG. 12 is similar to that shown in FIGS. 6 and 7 and the mechanism shown in FIG. 13 is similar to that shown in FIGS. 8 and 9.

Figure 14:
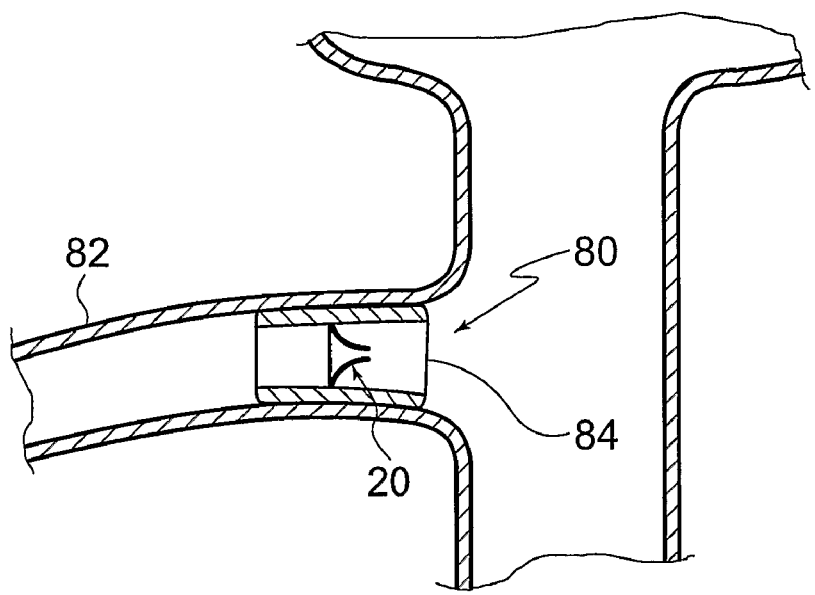
FIG. 14 is a cross sectional side view of a sixth embodiment of a device for treating heart failure implanted in a patient's hepatic vein.

FIG. 14 is a cross sectional side view of a sixth embodiment of a device 80 for treating heart failure, implanted in a patient's hepatic vein 82. The device 80 does not include any mounting flanges and its body is instead an expandable stent 84 with a one way valve 20 therein.

Figure 15:
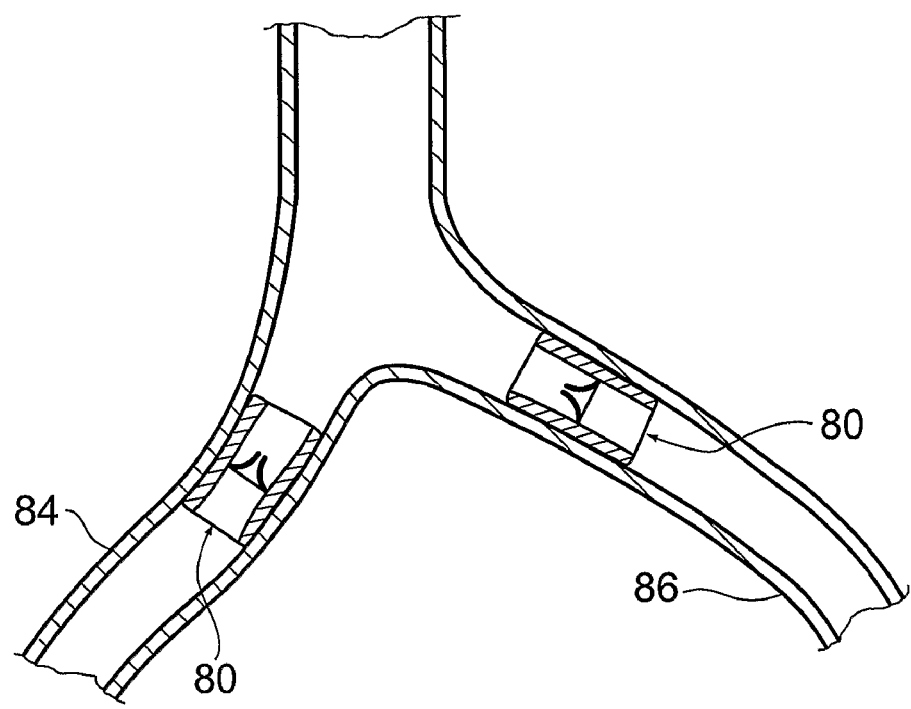
FIG. 15 is a cross sectional side view of a pair of the devices shown in FIG. 14 implanted in a patient's iliac veins.

FIG. 15 shows an alternative implanting of the device 80 in a patient's iliac veins 84 and 86.

The device 80 is also suitable for placement in the venous system of the lower limb or iliac system to relieve the signs or symptoms of lower limb hypertension (e.g., peripheral oedema and/or varicose veins).

Figure 16:
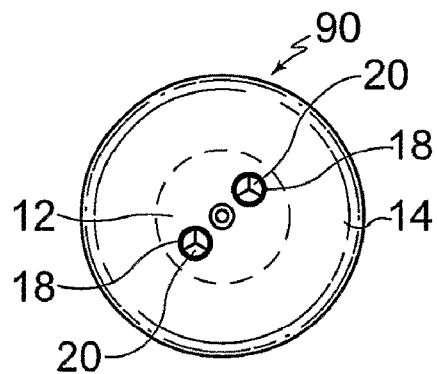
FIG. 16 is a front view of a seventh embodiment of a device for treating heart failure.

FIG. 16 shows a seventh embodiment of a device 90 for treating heart failure. The construction, function and implanting of the device 90 is similar to that of the device 40 and like reference numerals are used to indicate like features between the two embodiments. However, the device 90 has only two eccentrically located passages 18 through the body 12 and blood flow therethrough is controlled by two corresponding sets of valve leaflets 20.

Figure 17:
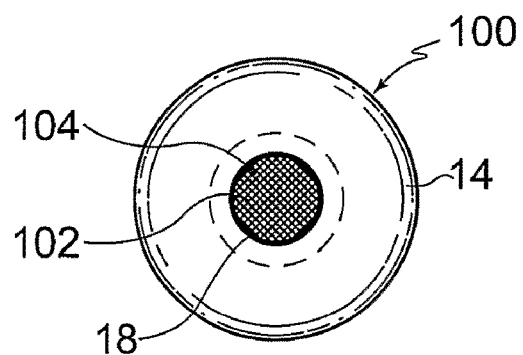
FIG. 17 is a front view of an eighth embodiment of a device for treating heart failure.
Figure 18:
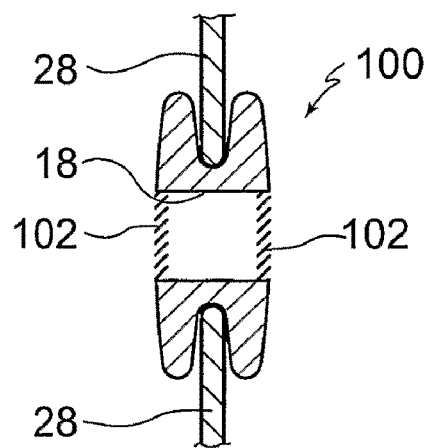
FIG. 18 is a cross sectional side view of the device shown in FIG. 17.

FIG. 17 shows an eighth embodiment of a device 100 for treating heart failure. This embodiment is constructed and implanted in a similar manner to that previously described. However, the device 100 has a passage 18 therethrough with a mesh or grill arrangement 102 across each end of the passage 18. The mesh 102 has apertures 104 therein of a maximum dimension of less than 4 mm which permit the flow of blood from the left to the right atrium through the passage 18, whilst substantially excluding thrombi. The mesh 102 is coated or impregnated with one or more drugs, adapted for preventing thrombosis or endothelialisation of the opening in the patient's atrial septum, including an anticoagulant substance, such as heparin, or an inhibitor of re-endthelialisation, such as sirolimus or paclitaxel.

FIGS. 19a and 19b show a ninth embodiment of a device 110 for treating heart failure. The construction, operation and implantation of the device 110 is similar to that of the device 10 and like reference numerals are used to indicate like features between the two embodiments. The device 110 utilizes a strut/fixture arrangement similar to that shown in FIGS. 6 and 7.

FIG. 20 shows a tenth embodiment of a device 130 for treating heart failure. The construction, operation and implantation of the device 130 is similar to that of the device 10 and like reference numerals are used to indicate like features between the two embodiments. The device 130 has a helical groove 132 for releasably engaging a corresponding fitting on the end of a catheter cable during implantation.

FIGS. 21a to 23b show an eleventh embodiment of a device 140 for treating heart failure. The construction, operation and implantation of the device 100 is similar to that of the device 10 and like reference numerals are used to indicate like features between the two embodiments. The body 12 and the flanges 14 of the device 140 are formed from a Nitinol wire mesh which result in it being suitable for implanting in a manner similar to the implanting of the AMPLATZER (Trade Mark) septal occluder produced by AGA Medical Corp. The device 140 is collapsed by pulling the exterior faces of the flanges 14 away from one another which causes the device 140 to lengthen and simultaneously reduce in diameter. When the separating force is removed the flanges 14 return to the (expanded) configuration.

Figure 21A:
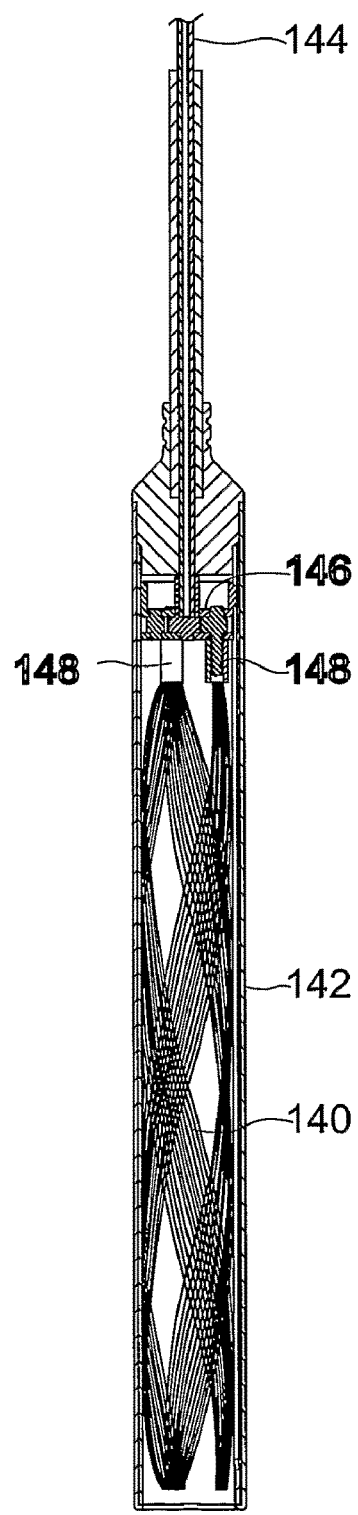
FIG. 21a is a cross sectional side view of an eleventh embodiment of a device for treating heart failure, collapsed within a catheter.
Figure 21B:
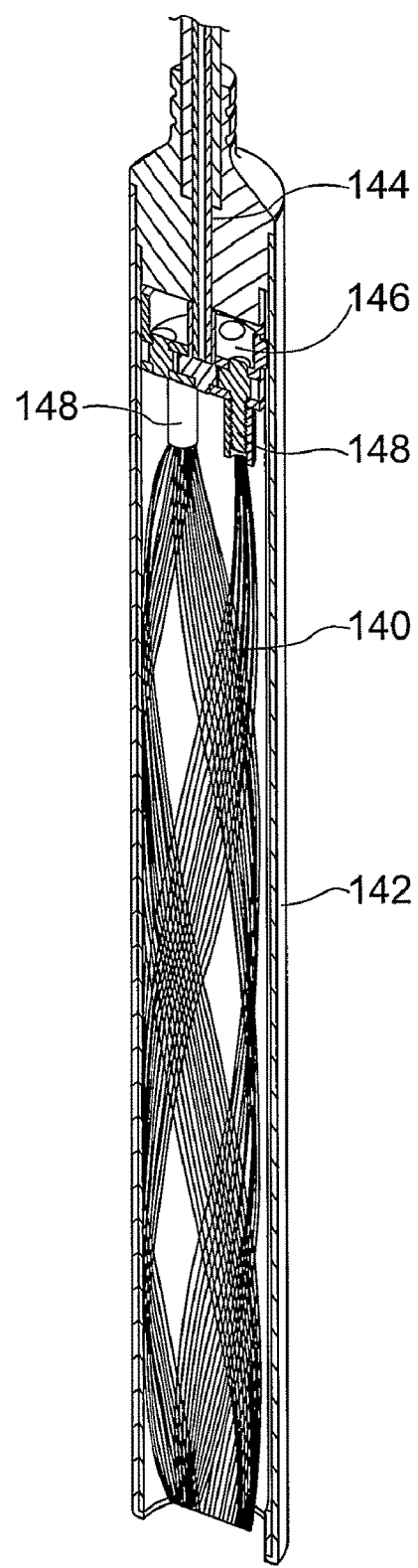
FIG. 21b is a cross sectional perspective view of the device shown in FIG. 21a, collapsed within a catheter.
Figure 22A:
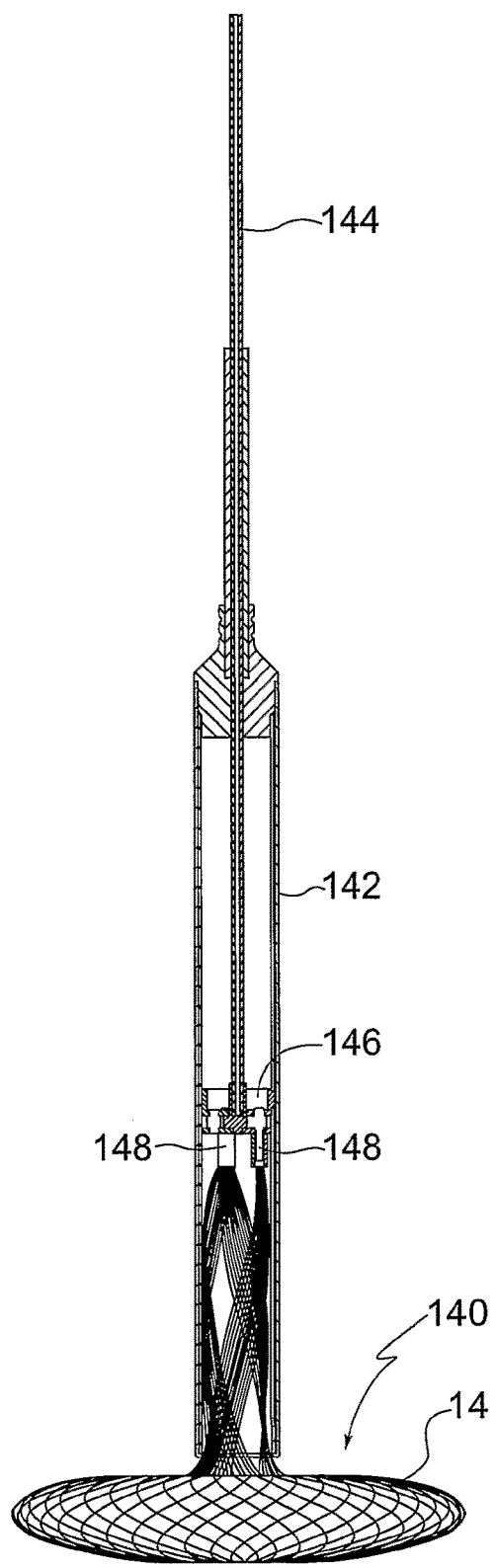
FIG. 22a is a cross sectional side view of the device shown in FIG. 21a, partially deployed from the catheter.
Figure 22B:
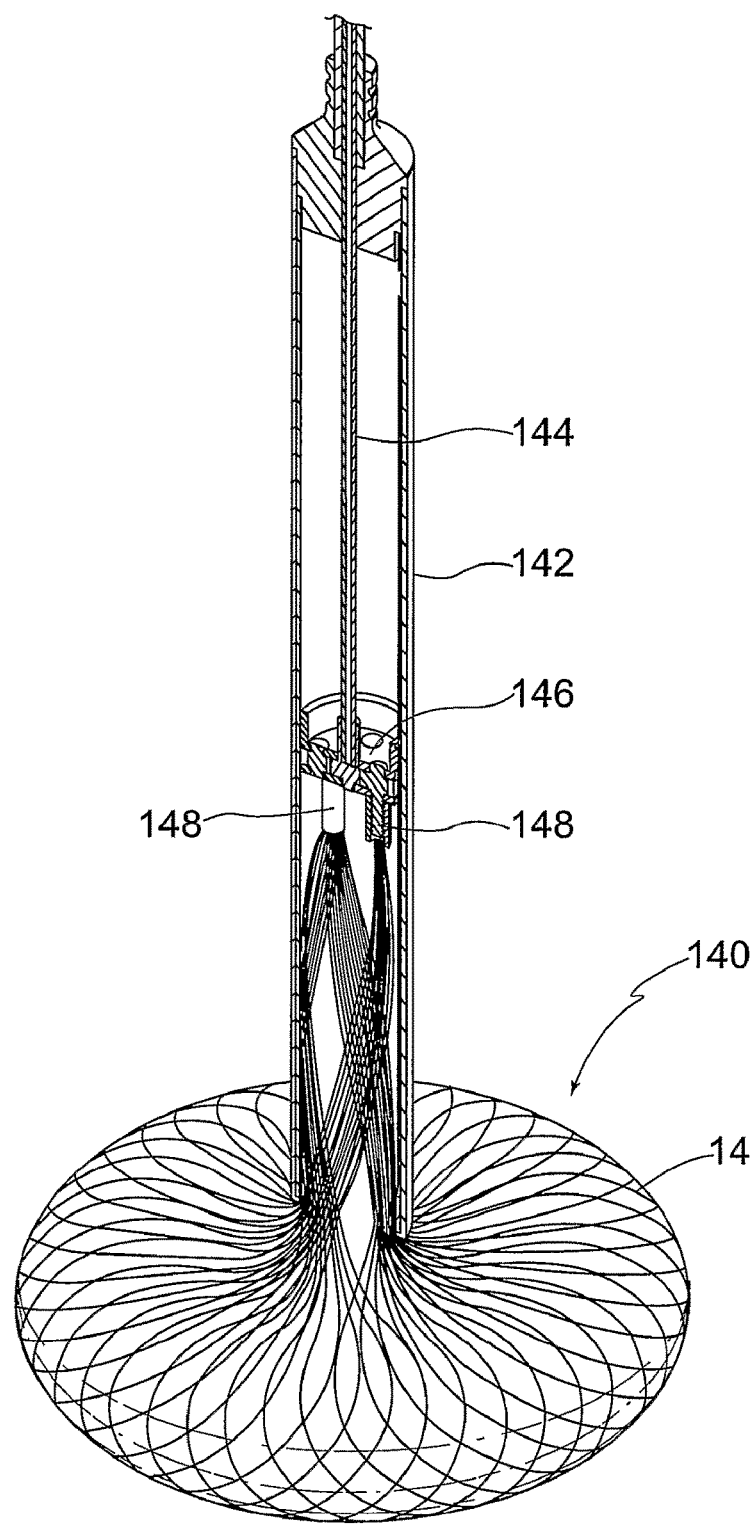
FIG. 22b is a cross sectional perspective view of the device shown in FIG. 21a, partially deployed from the catheter.
Figure 22C:
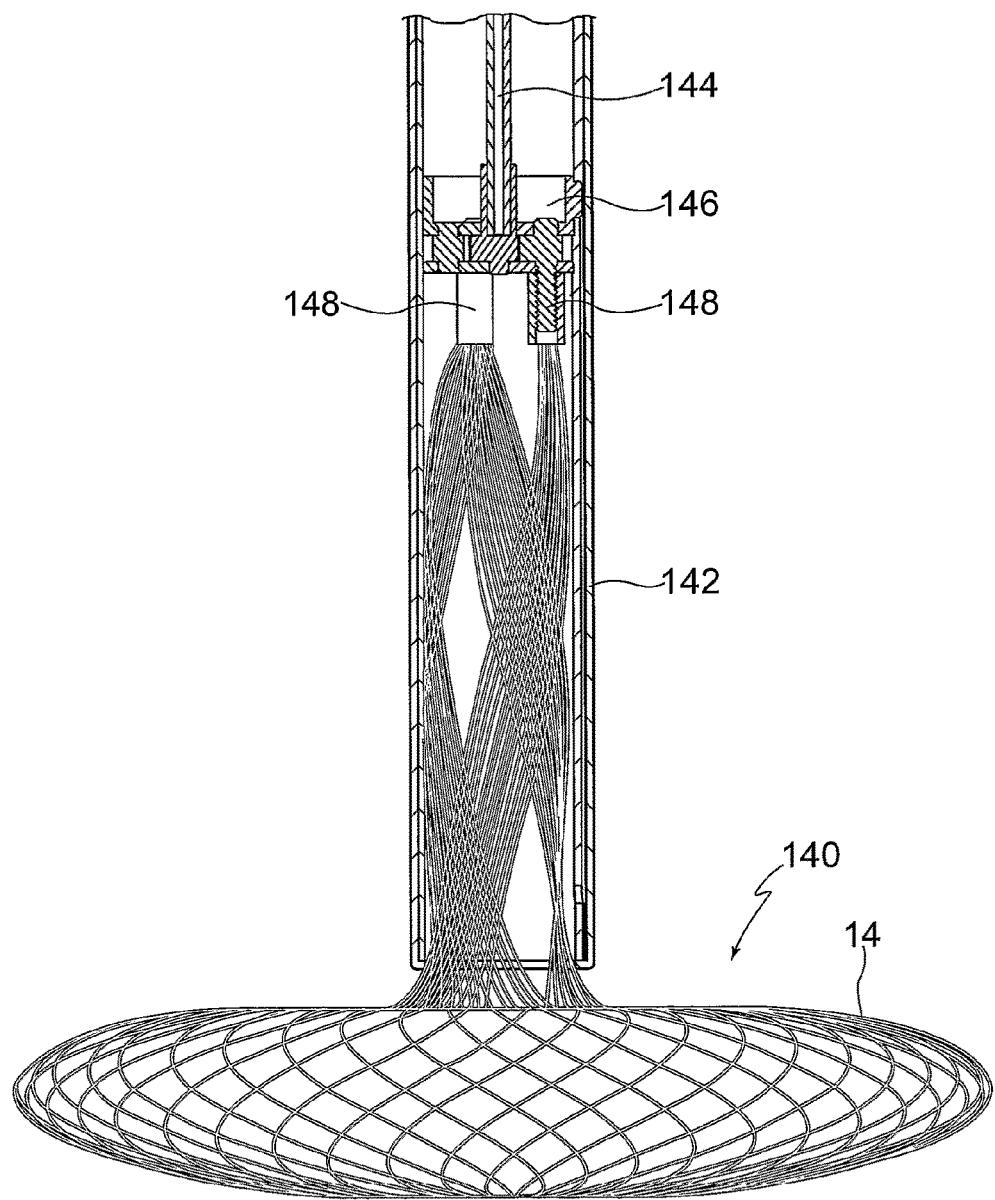
FIG. 22c is an enlarged, partial cross sectional side view of the device shown in FIG. 21a, partially deployed from the catheter.

More particularly, as shown in FIGS. 21*a* and 21*b*, the device 140 is initially collapsed within a catheter 142 of about 5 mm in diameter, which is able to pass through an opening in the septum. As shown in FIGS. 22*a* to 22*c*, the device 140 is then partially deployed from the catheter 142 by movement of wire 144, and thus head 146, relative to the catheter 142. This results in part of the device 140 expanding to form the first flange 14.

Figure 23A:
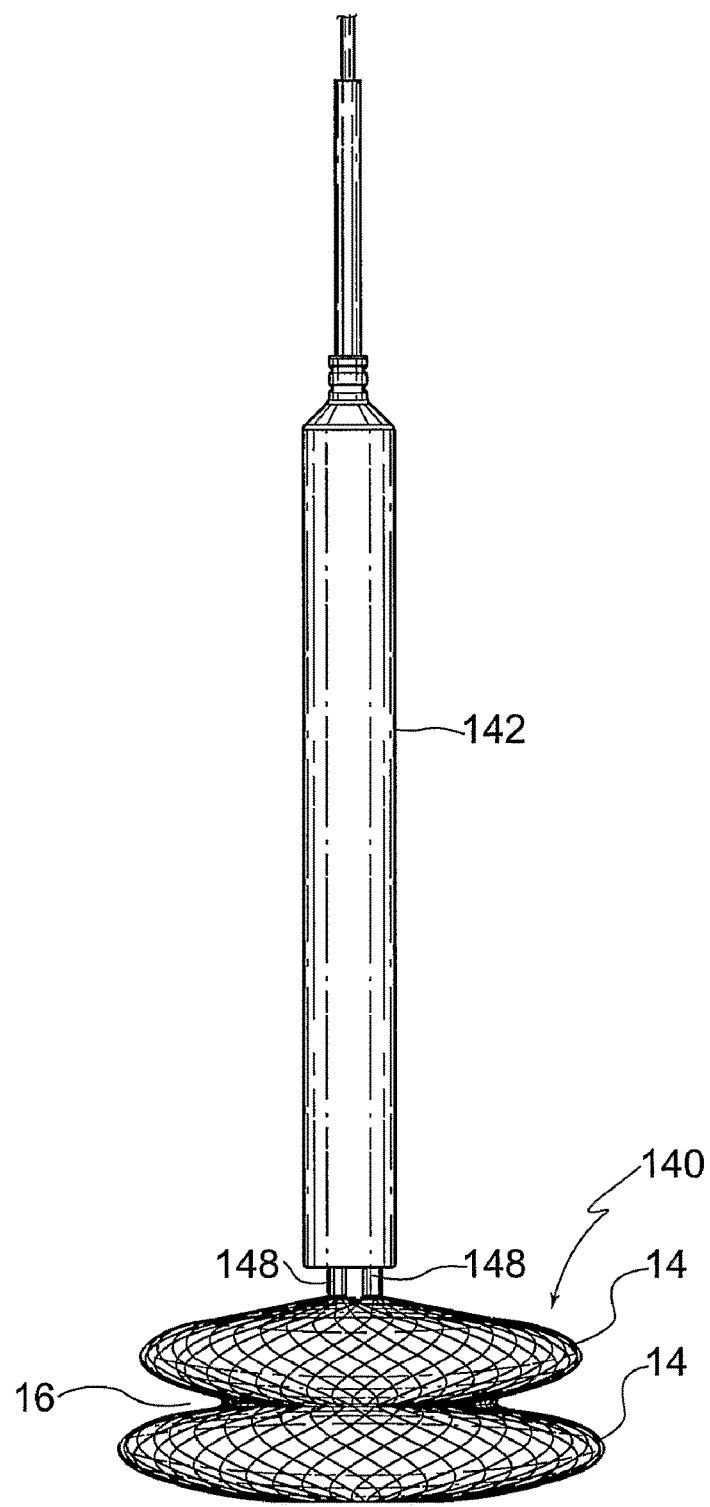
FIG. 23a is a side view of the device shown in FIG. 21a, deployed from the catheter.
Figure 23B:
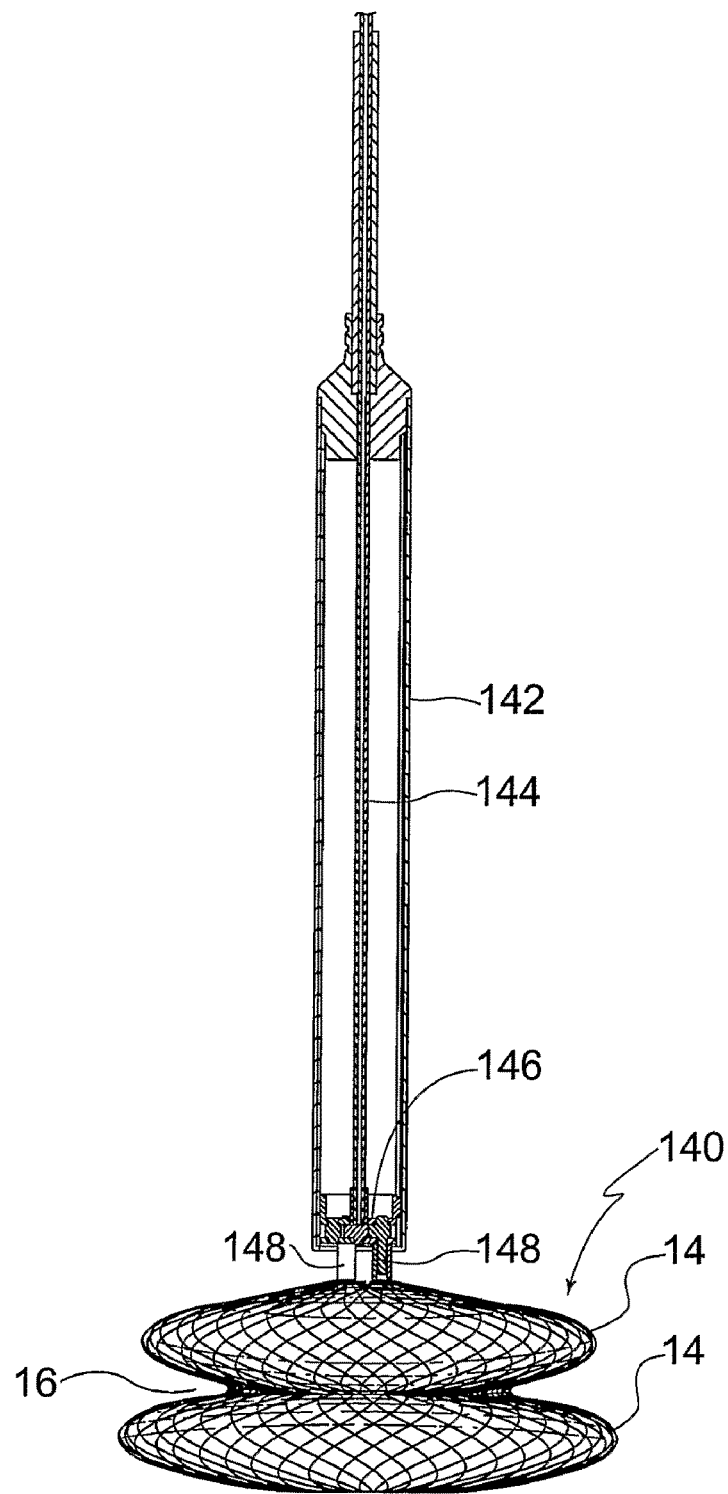
FIG. 23b is a cross sectional side view of the device shown in FIG. 21a, deployed from the catheter.
Figure 24:
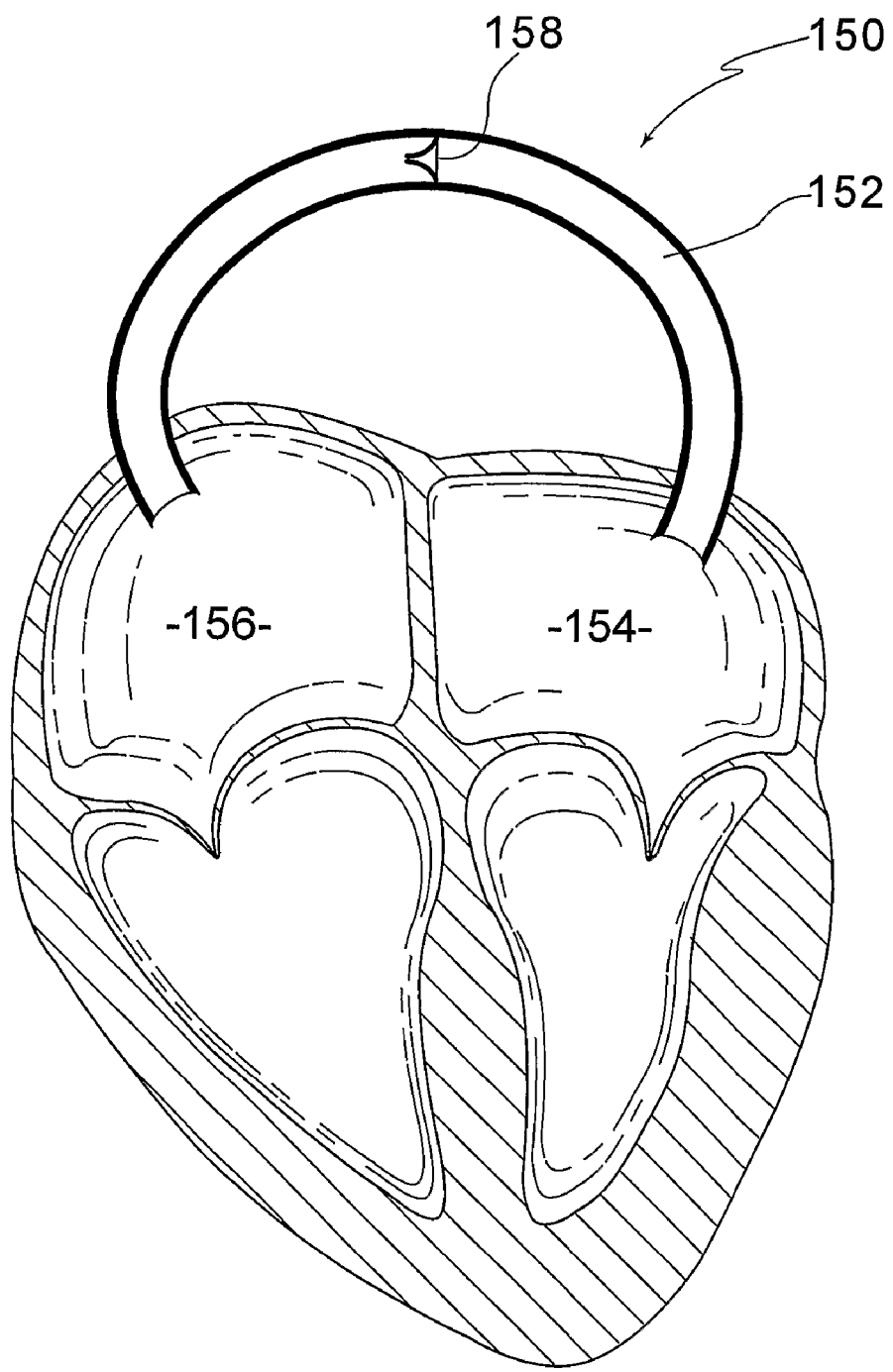
FIG. 24 is a cross sectional side view of a twelfth embodiment of a device for treating heart failure.

As shown in FIGS. 23*a* and 23*b*, fall deployment of the device 140 by further relative movement of the wire 144 and the head 146, relative to the catheter 142, results in the remainder of the device 140 expanding to form the second flange 14. The device 140 is initially attached to the head 146 by three pins 148, which are remotely released after the device has been deployed from the catheter 142.

In other similar embodiments (not shown) the catheter 142 has a diameter of 4-6 mm and the device 140 is initially attached to the head 146 by one or two releasable pins 148.

FIG. 20 shows a twelfth embodiment of a device 150 for treating heart failure. In this embodiment, a tube 152 of about 8 mm internal diameter provides an external fluid communication path between the heart's left and right atriums 154 and 156 respectively. A valve 158 is adapted to selectively occlude the tube 152. As with earlier embodiments, when the left atrial pressure exceeds the right atrial pressure by about 5-15 mm Hg, the valve 158 is released to open the interior of the tube 152 and allow blood flow from the left atrium 24 to the right atrium 26. In a variation of this embodiment, the valve 158 is a one way valve that prevents blood flow from the right atrium 156 to the left atrium 154.

Although the invention has been described with reference to the specific examples it will be appreciated by those skilled in the art that the invention may be embodied in many other forms.

What is claimed is:

1. A device for treating a heart condition in a patient, the device comprising: a body adapted and configured to self-expand from a radially collapsed configuration to an expanded configuration, the device in its expanded configuration comprising a first section and a second section, wherein each of the first and second sections has a first end and a second end, and the first ends of both first and second sections join together and wherein the first and second sections each have diameters that gradually increase with distance from their first ends towards their second ends, and wherein the device in its expanded configuration also has an annular gap between first and second sections of the device, the first ends of the first and second sections positioned at a midpoint of the annular gap, and wherein the body has a centrally located passage extending through the first and second sections, the passage having a diameter of about 4-15 mm, the body being configured to be delivered percutaneously to a patient's heart and allowed to self-expand in an opening in a septum of the heart to dispose the first section in the left atrium, the second section in the right atrium and the passage of the body to permit blood to flow from the left atrium to the right atrium.

2. The device of claim 1, further comprising a valve disposed in the body.

3. The device of claim 2, further comprising structure supporting the valve in the body.

4. The device of claim 2, wherein the valve is biased to a closed position.

5. The device of claim 4, wherein the valve is configured to open when pressure differential between the left atrium and the right atrium is 2 mm Hg or greater.

6. The device of claim 1, wherein the body comprises braided mesh.

7. The device of claim 1, wherein the first and second sections are sized and configured to engage the septum at the opening when the body is expanded in the opening.

8. The device of claim 1, wherein the body is elongated in the radially collapsed configuration.

* * * * *